US005531102A

United States Patent [19]
Brookfield et al.

[11] Patent Number: 5,531,102
[45] Date of Patent: Jul. 2, 1996

[54] VISCOMETER USABLE IN SITU IN LARGE REACTOR VESSELS

[75] Inventors: David A. Brookfield, Sharon; Robert P. Bishop, Pembroke, both of Mass.

[73] Assignee: Brookfield Engineering Laboratories, Inc., Stoughton, Mass.

[21] Appl. No.: 355,702

[22] Filed: Dec. 14, 1994

[51] Int. Cl.⁶ .................................................. G01N 11/14
[52] U.S. Cl. ......................... 73/54.32; 73/54.28; 73/54.23
[58] Field of Search ................................. 73/54.32, 54.23, 73/54.28

[56] References Cited

U.S. PATENT DOCUMENTS

| | | | |
|---|---|---|---|
| 2,491,639 | 12/1949 | Bechtel et al. | 73/54.32 |
| 2,957,339 | 10/1960 | Penny et al. | 73/54.28 |
| 4,594,883 | 6/1986 | Pollard | 73/54.23 |
| 5,167,143 | 12/1992 | Brookfield | 73/54.23 |

FOREIGN PATENT DOCUMENTS 1045467  10/1966  United Kingdom .................. 73/54.23

*Primary Examiner*—Hezron E. Williams
*Assistant Examiner*—Daniel S. Larkin
*Attorney, Agent, or Firm*—Jerry Cohen

[57] ABSTRACT

A viscometer (10) has a spindle (12) mounted on a rotatable shaft (14) which is, in turn, contained in a tubular rotatable shaft (16) which is within a fixed hollow shaft (18). The latter is suspended from a flange (20) that mates with a flange (22) of an access port (24) of a reactor vessel (RV). There is a base for an external tower (21) that carries a motor (M) and gearing (G) to drive the rotatable shafts (14, 16). A torque interconnection between the rotatable shafts allows angular deflection between them and a transducer (28) picks up such deflection.

23 Claims, 1 Drawing Sheet

VISCOMETER USABLE IN SITU IN LARGE REACTOR VESSELS

BACKGROUND OF THE INVENTION

The present invention relates to viscometers that are usable in situ in large reaction vessels for real time measurement of viscosity of liquids while undergoing chemical reaction or like process conditions.

The art of viscosity measuring has many products for laboratory or industrial off-line measurement of samples and a few for in-line (e.g. in piping or small vessels) measurement, e.g. the TT200 Process Viscomcter of Brookfield Engineering Laboratories, Inc., which has a viscosity range of 10–500,000 cps, shear rate range of 1 to 1,000 sec.$^{-1}$, and a pressure range of 0–200 psi. However, it has a working end length on the order of one foot. There is a need for a viscosity measuring instrument that can be mounted on a standard access port flange and inserted into a reaction vessel (e.g. for polymerization, cooking or boiling, compounding, mixing, thickening, solvating, saponification, reduction, etc.), with a working end of the instrument within the vessel substantively in excess of three feet, typically in the five to fifteen foot range.

It is an object of the invention to meet the foregoing needs and at the same time meet requirements of: (a) being top-mountable or side-mountable on reactor vessels; (b) withstanding high side loading against spindle and shaft; (c) having very low maintenance requirements; (d) withstanding vessel cleanings while installed; (e) being easily clearable while in the vessel (i.e. no special purge fittings and the instrument being clearable as the inside of the vessel is flushed); (f) withstanding all vessel operating conditions (temperature, pressure); (g) being suitable for explosion proof applications; (h) being easily removable from the vessel even when the length of the instrument's working end is on the order of ten to twelve feet long; (i) being fail-safe to prevent parts from falling into the vessel ( e.g., due to an overtorque situation); (j) being highly sensitive to viscosity changes during reaction; (k) being extremely repeatable under the same operating conditions; and (1) maintaining accuracy under all process operating conditions.

SUMMARY OF THE INVENTION

These requirements are met, according to the present invention, in a viscomelet that utilizes two elongated concentric simultaneously driven shafts one of them (preferrably the innermost one) mounting a viscosity pickup piece such as a spindle and deflecting rotationally relative to the other shafts as a result of viscous drag encountered in tile vessel. The shafts have a torque responsive interconnection of tile same type as the above cited TT200 instrument and a readout wire therein that is twisted in an angular deflection corresponding to shear effect on the measured fluid of the rotating end piece of the inner shaft. That deflection is picked up by a transducer and the electrical signal obtained therefrom can be fed to a display, data log device and/or process controller.

The above mentioned concentric shafts are in turn held in a further fixed hollow shaft (i.e. a third tube) that surrounds and supports the outer of tile first two shafts via axially spaced radial contacts over a considerable length, i.e. at least 20% of the axial length of the outer rotating shaft. An innermost one of such contacts is preferrably a bearing with a seal for resisting penetration by vessel liquids and gasses. The outermost of such contacts is a bearing which provides axial support for the rotating portions in addition to radial alignment. The said 'third' shaft could be a single tube or multiple tubes or a tubular cage or yoke or a helical coil spring or a variety of equivalents to a tube. It is, in any event, preferrably mounted from a flange or the like and insertable through a vessel access port and surrounds and supports portions of the instrument mounted from the port.

Other objects, features and advantages will be apparent from the following detailed description of preferred embodiments taken in conjunction with the accompanying drawings in which:

DETAILED DESCRIPTION OF PREFERRED EMBODIMENTS

Figure 1:
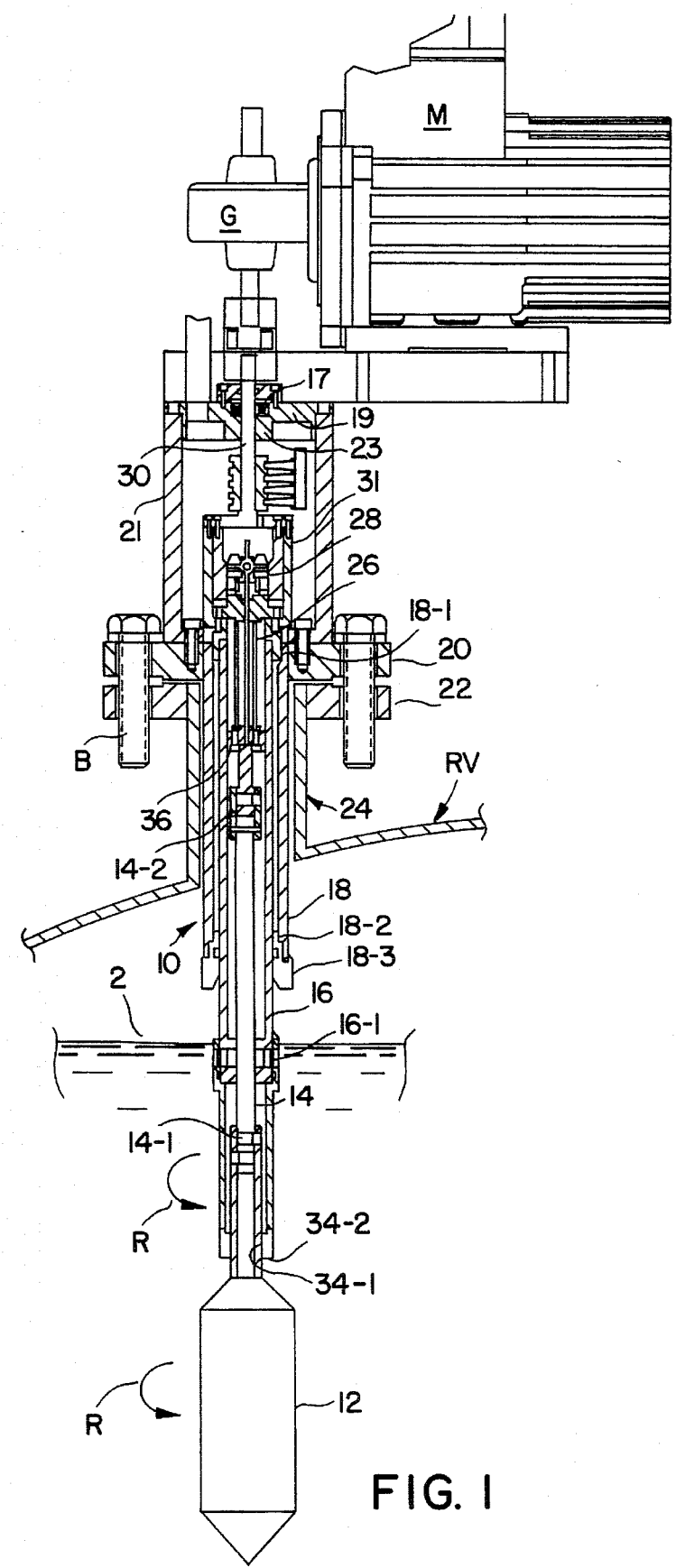
FIG. 1 is a cross-section view of a preferred embodiment of the invention as inserted into a reactor vessel, a breakaway portion of which is shown.

As shown in FIG. 1, the instrument 10 comprises a spindle 12 mounted on a (solid or hollow) shaft 14 which is contained within a tubular shaft 16 over a common axial length of 14 and 16 over a substantial axial distance, preferrably greater than 50% of the length of shaft 14. These are in turn within a fixed hollow shaft 18 (the said third shaft) that is suspended from a flange 20 that mates with a flange 22 of an access port 24 of a reactor vessel RV. An O-ring or gasket seal (not shown) can be provided between flanges 20 and 22 inside a ring array of bolts B. A tower 21 built on flange 20 carries a motor M and gearing G which drive a shaft 30 which, through a yoke 31, drives the shaft 16. The latter is interconnected to shaft 14 via a torque responsive cage array interconnection 26. The latter is of conventional torque interconnector form for viscometers of the type exemplified by the TT200 instrument, excepting that a block 36 is provided which has a tight bouncing clearance to the inner wall of tube 16 so that minimal radial deflection, if any, of block 36 relative to tube 16 occurs. A cap 19 on tower 21 has a bearing 17 and journal 23 for shaft 30. A narrow clearance seal may be provided at the tops of shafts 16, 18, within the tower externally of the reactor vessel (RV), as indicated at 18-1. A needle bearing or the like is provided at 18-2 and a rotary sliding seal at 18-3.

Interconnections for sections of shaft 14 are provided at. 14-1 and 14-2 and a similar interconnect for sections of shaft 16 is indicated at 16-1. The lengths of shafts 14 and 16 can thus be varied by inserting selected numbers and lengths of pieces for different lengths of insertion to or into a liquid of the vessel (having a level L). One or more such connections, as shown at 16-1, can also provide a means of further stabilizing the concentric arrangement of 14 and 16 with a loose sliding fit tube between.

A radial support structure (34-1), such as a bearing surface similar to 36 or a bushing or a ball bearing, positioned at the lower end of shaft 16 and as close to spindle 12 as practical, completes the stabilization of shafts 14, 16 as they rotate in common (arrows R). A flex type of O-ring seal 34-2 is provided to prevent reactor vessel contents from penetrating the space between shafts 14, 16. The seal is selected to allow no slippage with respect to the two shafts abutting it and contributes a torque less than 10% of the torque due to fluid shear.

There is no baffle tube around spindle 12 or the inserted ends of shafts 14, 16, 18.

Having the spindle totally exposed in the vessel fluid permits optimal cleanability, and at the same time minimizes the effect, that any build up on the spindle surface over time will have on instrument accuracy.

In order to minimize the effect of internal flows within the reactor vessel, the spindle is rotated at relatively high speeds thereby creating a controlled shear rate at the spindle surface that is substantially independent of the much lower shear rates due to mixing, etc. of the reaction fluid.

Because there is very little relative motion between the intermediate tube 16 and the inner shaft 14 (a maximum of one degree at full scale deflection), the seal 34-2 can be designed such that the O-ring flexes, but the shaft does not actually slip within it. This aids accuracy and repeatability as well as allowing a more complete resistance to fluid penetration into the annulus between 14 and 16. The O-ring cap is designed so there is a wide gap between the cap and the spindle shaft, to prevent material from building up and bridging across to the shaft. The O-ring seal may be made of DuPont's Kalrez brand perfluoro-eslastomer (or the like) to meet application requirements. It is necessary to assure minimal torque contribution from the "O"-ring deflection consistent with proper sealing.

The block 36 on the bottom of the torsion element is designed to have very little clearance to the inner wall of the intermediate tube. This will act as an upper bearing for the shaft 14 if side loading on the spindle 12 is extreme. Because the structure is turning, the flange will continually break contact with the tube wall, so adverse effect on the output signal will be negligible. This same mechanism can be used at the lower (spindle) end of the intermediate shaft 16 to eliminate bearing friction altogether, if necessary.

The tube diameters and wall thicknesses are selected to maintain straight alignment of the spindle and the torsion element under operating conditions. Misalignment (bending) of the shaft due to mixing and flows in the vessel causes a loss of torque signal from the spindle and consequently a loss in accuracy.

Three concentric tubes (14, 16, 18) are used to reach the required spindle shaft length. The innermost tube (which could also be a solid rod for all or part of its length) runs directly from the torsion element to the spindle. The intermediate tube is intended to add stiffness to the structure by supporting the spindle shaft near the spindle itself and to limit exposure of the innermost tube above the spindle which can cause unwanted torque contributions from the fluid. This intermediate tube is the part driven by the motor M. The outer tube supports the intermediate tube with a bearing part way down the shaft. The long axial length overlap of the first and second shafts (14, 16) within the reactor vessel is at least two feet and, as noted above, at least half the length of the first shaft (14).

The outer tube 18 is made as long as feasible, but its length is such that it will be above the level L of the liquid in the vessel in most vessel conditions. The bearing 18-2 is protected from vapors and splashing by lip seal 18.3. Drag a sliding seal position has no effect on measurement.

The intermediate tube 16 will in some applications be immersed in the fluid. A large cross-section O-ring is at the bottom of the tube to protect the bearing and other internal parts from fluids or vapors. The design of the O-ring and cap is critical, because the signal can be affected by excess drag or by build-up of the process material on shaft 14.

The three concentric tubes are designed to keep the structure as stiff as possible to resist the side loadings inherent in the process. The support points on both the outer and intermediate tubes are brought down as low as practical in each application. As mentioned above, the inner shaft, and intermediate tube can each be segmented for applications requiring long probes. Break points are not always necessary in the shorter instruments.

Vertical stops may be built into the instrument to prevent the spindle shaft or intermediate tube from falling into the vessel. Raised portions that act as stops are left on these shafts above the bearings when the outside diameters of the tubes are machined, or parts such as collars or set screws could be added. The lip seal cap and tube segment have angled surfaces so any process material will run off the instrument, rather than build up on flat surfaces.

The transducer 28 can be located above the mounting flange 20; this allows for higher temperature applications than if the transducer was inside the tubes, down in the vessel.

Damping fluid can be used to fill the annulus between 14 and 16 and/or the annulus between 16 and 18 to minimize vibration without adding a spurious measured parameter.

The instrument can be left inside the vessel during cleanings. In some applications, multiple batches are run between cleanings. In this case, material will flow off the instrument while liquid. Solidified material will melt into the next batch. The design is such that slight build-up will not affect the output of the device, due to careful seal and spindle designs of the nature indicated above. Filling vessel RV with solvent to clean its walls can also serve to clean exposed surfaces of 12, 14, 16, 18. Yet the assembly 12, 14, 16, 18 is easily removable through port 24 to change shaft lengths, change seals, perform other off line cleaning, maintenance, or recalibration and is then easily reinsertable.

It will now be apparent to those skilled in the art that other embodiments, improvements, details, and uses can be made consistent with the letter and spirit of the foregoing disclosure and within the scope of this patent which is limited only by the following claims, construed in accordance with the patent law, including the doctrine of equivalents.

What is claimed is:

1. A viscometer for insertion into a reactor vessel or the like comprising:

(a) means defining a first elongated shaft extending from the proximal position outside the vessel to a distal position with a measuring surface at the distal end and means for rotating the shaft with the distal end within contents of the vessel, (b) means defining a second shaft which is tubular and surrounds the first shaft over a common axial length portion thereof, the first and second shafts being essentially concentric and having means to respond correctively to radial deviation of either or both of the shafts from concentricity without imposing substantial rotational drag therebetween, (c) means for interconnecting the shafts for rotation in common, said means including a torque responsive interconnect allowing angular deflection between the connected shafts responsive to shearing force sensed at said measuring surface element, (d) means responsive to such angular deflection to yield an output, (e) means for stabilizing the first and second shafts to remain aligned with a selected concentric axis thereof, (f) means for mounting a majority length portion of the first and second shaft within the said reactor vessel or the like and for mounting a drive system for the first and second shafts outside the vessel.

2. Viscometer in accordance with claim 1 wherein the said torque interconnection between the first and second shafts is also mounted outside the vessel.

3. Viscometer in accordance with either of claims 1 or 2 wherein the first and second shaft portions within the vessel have a length of at least two feet, the said axial length of axial overlap of the first and second shafts being at least 50% of the length of the first shaft and including a portion of the first shaft adjacent to the measuring surface element.

4. Viscometer in accordance with claim 3 wherein such length exceeds five feet.

5. Viscometer in accordance with claim 3 wherein said length is at least eight feet.

6. Viscometer in accordance with claim 3 wherein at least one of the first and second shafts comprises multiple connected portions.

7. Viscometer in accordance with claim 6 wherein both such shafts comprise multiple connected portions.

8. Viscometer in accordance with claim 3 wherein a flexing seal is provided at a distal (from the drive) end of the second shaft to bridge to the first shaft.

9. Viscometer in accordance with either of claims 1 or 2 wherein at least one of the first and second shafts comprises multiple connected portions.

10. Viscometer in accordance with claim 9 wherein both such shafts comprise multiple connected portions.

11. Viscometer in accordance with either of claims 1 or 2 wherein a flexing seal is provided at a distal (from the drive) end of the second shaft to bridge to the first shaft.

12. Viscometer in accordance with claim 8 wherein the flexing seal is an O-ring of sufficient cross section relative to its inner diameter that no slippage occurs between the flexing seal and the shafts.

13. Viscometer in accordance with claim 12 wherein the torsional contribution of the seal is less than 10% of torque due to fluid shear.

14. Viscometer in accordance with either of claims 1 or 2 wherein said means for stabilizing (e) and mount (f) comprise a means for mounting securable to an outer vessel wall and a third shaft which is hollow, fixed and suspended from the mount, and passes through an opening of the vessel wall and is arranged essentially concentrically with said rotating second shaft and further comprising spaced axial means to prevent shift of the common axis of the second and third shafts.

15. Viscometer in accordance with claim 14 wherein the spaced axial means are partly within the envelope of the vessel and partly outside it.

16. Viscometer in accordance with claim 15 and further comprising a rotary seal between the third and second shafts.

17. Viscometer in accordance with either of claims 1 or 2 wherein the drive for the first and second shafts comprises a cylindrical yoke.

18. Viscometer in accordance with claim 17 wherein said deflection response means are positioned within the yoke.

19. A viscometer for insertion into a reactor vessel or the like comprising:

(a) means for rotating within contents of the vessel, and including a measuring surface element mounted at the distal end of a first elongated shaft, (b) means defining a second shaft which is tubular and surrounds the first shaft over a long axial length which is at least 50% of the length of the first shaft and includes a portion of the first shaft adjacent the measuring surface element, the first and second shafts being essentially concentric and having means to respond correctively to radial deviation of either or both of the shafts from concentricity without imposing substantial rotational drag therebetween, (c) means for interconnecting the first and second shafts for rotation in common, said means including a torque responsive interconnect allowing angular deflection between the connected shafts responsive to shearing force sensed at said measuring surface element, (d) means responsive to such angular deflection to yield an output, (e) means for stabilizing the first/second shaft array to remain aligned with a selected concentric axis thereof, and (f) means for mounting a majority length portion of the first/second shafts within a reactor vessel or the like.

20. Viscometer in accordance with claim 19 wherein at least the elements (a)–(c) are insertable and removable into and from the vessel via an access port.

21. Viscometer in accordance with claim 20 further comprising a third fixed shaft surrounding an axial portion of the said second shaft and being also insertable and removable with the first/second shafts via an access port.

22. A viscometer in accordance with any of claims 19, 20 or 21 wherein any portions of the instrument exposed to reactor vessel liquid or vapor are mounted on a mounting flange which is mate able with a flange of the access port.

23. A viscometer in accordance with claim 22 and further comprising a tower mounted on said mounting flange externally of the reactor vessel and containing components of the first/second shafts drive, said interconnection and transducer means for picking up and transducing an output signal corresponding to relative deflection between the first and second shafts.

* * * * *